United States Patent
Utsumi et al.

(10) Patent No.: US 7,601,667 B2
(45) Date of Patent: Oct. 13, 2009

(54) SULFONATE CATALYST AND METHOD OF PRODUCING ALCOHOL COMPOUND USING THE SAME

(75) Inventors: Noriyuki Utsumi, Soka (JP); Kunihiko Murata, Koshigaya (JP); Kunihiko Tsutsumi, Tokyo (JP); Takeaki Katayama, Soka (JP); Masahito Watanabe, Soka (JP); Takeshi Ohkuma, Sapporo (JP); Ryoji Noyori, Tokyo (JP)

(73) Assignees: Kanto Kagaku Kabushiki Kaisha, Tokyo (JP); Nagoya Industrial Science Research Institute, Nagoya-shi (JP)

( * ) Notice: Subject to any disclaimer, the term of this patent is extended or adjusted under 35 U.S.C. 154(b) by 0 days.

(21) Appl. No.: 11/922,409

(22) PCT Filed: Mar. 10, 2006

(86) PCT No.: PCT/JP2006/304750

§ 371 (c)(1),
(2), (4) Date: Feb. 8, 2008

(87) PCT Pub. No.: WO2006/137195

PCT Pub. Date: Dec. 28, 2006

(65) Prior Publication Data

US 2008/0234525 A1 Sep. 25, 2008

(30) Foreign Application Priority Data

Jun. 20, 2005 (JP) .............................. 2005/011679

(51) Int. Cl.
*B01J 31/18* (2006.01)
*B01J 31/12* (2006.01)
*C07C 29/145* (2006.01)

(52) U.S. Cl. ....................... 502/166; 502/167; 568/862; 568/881

(58) Field of Classification Search ................. 502/166, 502/167; 568/862, 881
See application file for complete search history.

(56) References Cited

U.S. PATENT DOCUMENTS

| | | |
|---|---|---|
| 2002/0173683 A1 | 11/2002 | Chen |
| 2004/0220165 A1 | 11/2004 | Thomas et al. |
| 2005/0107621 A1 | 5/2005 | Takehara et al. |

FOREIGN PATENT DOCUMENTS

| | | |
|---|---|---|
| EP | 1 346 972 A1 | 9/2003 |
| JP | A-8-225466 | 9/1996 |
| JP | A-11-322649 | 11/1999 |
| JP | A-2003-104933 | 4/2003 |
| JP | A-2004-155756 | 6/2004 |
| JP | A-2004-522732 | 7/2004 |
| WO | WO 02/051781 A1 | 7/2002 |
| WO | WO 02/055195 A2 | 7/2002 |

OTHER PUBLICATIONS

J. Takehara et al., "Amino alcohol effects on the ruthenium(II)-catalysed asymmetric transfer hydrogenation of ketones in propan-2-ol," *Chem. Commun.*, 1996, pp. 233-234.

J. Gao et al., "A Ruthenium(II) Complex with a $C_2$-Symmetric Diphosphine/Diamine Tetrdentate Ligand for Asymmetric Transfer Hydrogenation of Aromatic Ketones," American Chemical Society, *Organometallics*, 1996, 15, pp. 1087-1089.

*Primary Examiner*—Elvis O Price
(74) *Attorney, Agent, or Firm*—Oliff & Berridge, PLC

(57) ABSTRACT

A sulfonate catalyst represented by the formula below and a ketone compound are placed in a solvent, and the ketone compound is hydrogenated by mixing in the presence of hydrogen to produce an optically active alcohol.

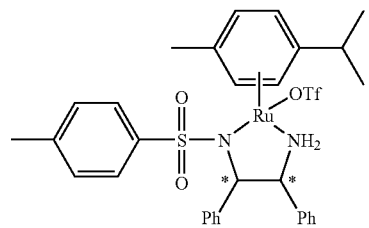

12 Claims, No Drawings

SULFONATE CATALYST AND METHOD OF PRODUCING ALCOHOL COMPOUND USING THE SAME

TECHNICAL FIELD

The present invention relates to a sulfonate catalyst and a method for producing alcohol compounds using the same.

BACKGROUND ART

There have been reported various methods for producing optically active alcohols using metal complexes as a catalyst. In particular, a method for synthesizing optically active alcohols from ketone compounds by a reductive process using a ruthenium complex as a catalyst in the presence of a base has been intensively researched.

With respect to asymmetric hydrogenation and a catalyst for producing optically active alcohols by asymmetric hydrogenation of ketones using hydrogen as a reducing agent, for example, Japanese Unexamined Patent Application Publication No. 8-225466 has reported an example in which an optically active alcohol was produced by hydrogenation of a ketone compound in the presence of a base, using a mixture of a complex, in which BINAP (2,2'-bis(diphenylphosphine)-1,1'-binaphthyl) and DMF coordinate to ruthenium, and diphenylethylenediamine as a catalyst.

However, a hydrogenation reaction does not efficiently proceed or an enantiomer excess may be insufficient depending on the structure of the ketone compound used. In the above-described catalyst system, a ketone compound unstable to a base and a ketone having acidic hydrogen cannot be hydrogenated because the reaction is effected under basic conditions. In order to solve this problem, some attempts have been made.

For example, Japanese Unexamined Patent Application Publication No. 2003-104993 has reported some examples in each of which an optically active alcohol was produced by hydrogenation of a ketone compound unstable to a base using as a catalyst tetrahydroborate salt of a chiral ruthenium metal complex containing a diphosphine compound, such as BINAP, and a diamine compound, which coordinate to ruthenium, in 2-propanol not containing a base under pressurized hydrogen. Specifically, ethyl 4-acetylbenzoate and 3-nonen-2-one are used for producing corresponding respective optically active alcohols.

However, the catalyst described in Japanese Unexamined Patent Application Publication No. 2003-104993 may exhibit low yield and low enantiomer excess depending on the reaction substrate used, and thus the structures of applicable ketone compounds are limited.

For catalytic asymmetric hydrogenation, many methods using an alcohol or formic acid as a reducing agent, i.e., catalytic asymmetric reduction reactions, have been reported. In particular, a chiral ruthenium catalyst (Japanese Unexamined Patent Application Publication No. 11-322649) having an amine ligand containing a sulfonylamide group as an anchor has noteworthy performance. There have been also reported similar catalyst systems (Chem. Commun. 1996, 223. Organometallics 1996, 15, 1087) each having a ruthenium-amine complex as a basic skeleton. Also, rhodium and iridium catalysts (J. Org. Chem. 1999, 64, 2186) each having a metal-amine bond have been reported. These chiral metal catalysts can asymmetrically reduce many kinds of ketone substrates as compared with the above-described hydrogenation catalysts. However, the activation ability of hydrogen is low, and only organic compounds such as 2-propanol and formic acid can be used as hydrogen sources. Therefore, the catalyst must be used in a larger amount than that for asymmetric hydrogenation with hydrogen. In addition, the use of formic acid has the problem of corrosion of a reaction kettle. Further, there has been reported asymmetric reduction of phenacyl chloride using formic acid as a reducing agent in the presence of a catalyst containing rhodium as a central metal. This reduction also has problems with catalytic activity and the use of corrosive formic acid. Therefore, there has been demand for asymmetric hydrogenation of various ketone substrates using hydrogen as a reducing agent with high enantioselectivity and high efficiency.

DISCLOSURE OF THE INVENTION

As described above, a conventional method using a hydrogenation catalyst has limitations to the structures of applicable ketone compounds and has the large problem of failing to efficiently produce alcohols with structures such as 2-chloro-1-phenylethanol and 4-chromanol and optically active alcohols thereof in spite of its industrial usefulness. On the other hand, there has been known a method of asymmetrically reducing ketones using formic acid as a reducing agent. However, this method has problems with efficiency because a large amount of the catalyst is used and corrosive formic acid is used.

The present invention has been achieved for solving the above-mentioned problems, and an object of the present invention is to provide a hydrogenation catalyst useful in producing an alcohol compound which could have not been easily obtained, and provide a method for producing an alcohol compound using the hydrogenation catalyst.

As a result of intensive research for achieving the object, the inventors have found that a group VIII or IX transition metal sulfonate complex containing an amine ligand can efficiently advance hydrogenation, particularly highly enantioselective hydrogenation, of a ketone substrate which cannot be easily hydrogenated with a conventional hydrogenation catalyst, resulting in the completion of the present invention.

The present invention provides a sulfonate catalyst represented by general formula (1) and used for a hydrogenation reaction.

General Formula (1)

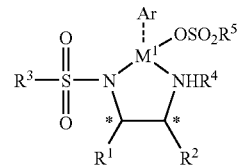

wherein $R^1$ and $R^2$ may be the same or different and each represent an alkyl group, a phenyl group, a naphthyl group, or a cycloalkyl group, which may be substituted, or a part of an alicyclic ring formed by bonding of $R^1$ and $R^2$;

$R^3$ represents an alkyl group, a phenyl group, a naphthyl group, or camphor which may be substituted;

$R^4$ represents a hydrogen atom or an alkyl group;

$R^5$ represents an alkyl group, a phenyl group, a naphthyl group, or camphor which may be substituted;

Ar is bonded to $M^1$ through a πbond and represents benzene which may be substituted or a cyclopentadienyl group which may be substituted;

$M^1$ represents ruthenium, rhodium, or iridium; and
* represents chiral carbon.

A method for producing an alcohol compound according to the present invention includes hydrogenating a ketone compound using the sulfonate catalyst to produce an alcohol compound. By using the sulfonate catalyst of the present invention, an alcohol compound which could have been not easily obtained can be produced.

BEST MODE FOR CARRYING OUT THE INVENTION

The present invention will be described in detail below.

With respect to a sulfonate catalyst of the present invention, examples of $R^1$ and $R^2$ in the general formula (1) include alkyl groups each having 1 to 10 carbon atoms, such as a methyl group, an ethyl group, a n-propyl group, an isopropyl group, a n-butyl group, a sec-butyl group, and a tert-butyl; a phenyl group; phenyl groups each including an alkyl group having 1 to 5 carbon atoms, such as a 4-methylphenyl group and a 3,5-dimethylphenyl group; phenyl groups each including a halogen substituent, such as 4-fluorophenyl group and a 4-chlorophenyl group; phenyl groups each including an alkoxy group, such as 4-methoxyphenyl group; a naphthyl group; a 5,6,7,8-tetrahydro-1-naphthyl group; a 5,6,7,8-tetrahydro-2-naphthyl group; a cyclopentyl group; and a cyclohexyl group. Also, $R^1$ and $R^2$ may be bonded together to form an unsubstituted or substituted alicyclic ring. Examples of such a ring include a cyclopentane ring and a cyclohexane ring. Among these groups, both $R^1$ and $R^2$ are preferably phenyl groups, or $R^1$ and $R^2$ are preferably bonded together to form a cyclohexane ring.

Examples of an alkyl group as $R^3$ in the general formula (1) include alkyl groups each having 1 to 10 carbon atoms, such as a methyl group, an ethyl group, a n-propyl group, an isopropyl group, a n-butyl group, a sec-butyl group, and a tert-butyl group. These alkyl groups may have a substituent, and, for example, may have one or more fluorine atoms as a substituent. Examples of the alkyl groups having one or more fluorine atoms include a fluoromethyl group, a difluoromethyl group, a trifluoromethyl group, and a pentafluoroethyl group. Examples of a naphthyl group which may be substituted include an unsubstituted naphthyl group, a 5,6,7,8-tetrahydro-1-naphthyl group, and a 5,6,7,8-tetrahydro-2-naphthyl group. Examples of a phenyl group which may be substituted include an unsubstituted phenyl group; phenyl groups each including an alkyl group, such as a 4-methylphenyl group, a 3,5-dimethylphenyl group, a 2,4,6-trimethylphenyl group, and a 2,4,6-triisopropyl phenyl group; phenyl groups each including a halogen substituent, such as a 4-fluorophenyl group and a 4-chlorophenyl group; and phenyl groups each including an alkoxy group, such as a 4-methoxyphenyl group.

Examples of $R^4$ in the general formula (1) include alkyl groups having 1 to 5 carbon atoms, such as a methyl group and an ethyl group, and a hydrogen atom. However, a hydrogen atom is preferred.

Examples of Ar in the general formula (1) include unsubstituted benzene, and benzenes each including one or more alkyl groups, such as toluene, o-, m- and p-xylene, o-, m-, and p-cymene, 1,2,3-, 1,2,4-, and 1,3,5-trimethylbenzene, 1,2,4,5-tetramethylbenzene, 1,2,3,4-tetramethylbenzene, pentamethylbenzene, and hexamethylbenzene. Examples of cyclopentadienyl group which may be substituted include a cyclopentadienyl group, a methylcyclopendadienyl group, a 1,2-dimethylcyclopentadienyl group, a 1,3-dimethylcyclopentadienyl group, a 1,2,3-trimethylcyclopentadienyl group, a 1,2,4-trimethylcyclopentadienyl group, a 1,2,3,4-tetramethylcyclopentadienyl group, and a 1,2,3,4,5-pentamethylcyclopentadienyl group (Cp*).

In the general formula (1), $M^1$ represents any one of ruthenium, rhodium, and iridium.

Examples of an alkyl group as $R^5$ in the general formula (1) include alkyl groups each having 1 to 10 carbon atoms, such as a methyl group, an ethyl group, a n-propyl group, an isopropyl group, a n-butyl group, a sec-butyl group, and a tert-butyl group. These alkyl groups may have a substituent, and, for example, may have one or more fluorine atoms as a substituent. Examples of the alkyl groups having one or more fluorine atoms include a fluoromethyl group, a difluoromethyl group, a trifluoromethyl group, and a pentafluoroethyl group. Examples of a naphthyl group which may be substituted include an unsubstituted naphthyl group, a 5,6,7,8-tetrahydro-1-naphthyl group, and a 5,6,7,8-tetrahydro-2-naphthyl group. Examples of a phenyl group which may be substituted include an unsubstituted phenyl group; phenyl groups each including an alkyl group, such as a 4-methylphenyl group, a 3,5-dimethylphenyl group, a 2,4,6-trimethylphenyl group, and a 2,4,6-triisopropyl phenyl group; phenyl groups each including a halogen substituent, such as a 4-fluorophenyl group and a 4-chlorophenyl group; and phenyl groups each including an alkoxy group, such as a 4-methoxyphenyl group. Among these groups, an alkyl group including one or more fluorine atoms is preferred, a perfluoroalkyl group is more preferred, and a trifluoromethyl group is particularly preferred.

The sulfonate catalyst represented by the general formula (1) is considered to have a structure in which a bidentate ethylenediamine compound ($R^3SO_2NHCHR^1CHR^2NHR^4$) is bonded to a metal. In order to more specifically disclose the sulfonate catalyst represented by the general formula (1), examples of the ethylenediamine compound are given below. Namely, the examples include N-(p-toluenesulfonyl)-1,2-diphenylethylenediamine (TsDPEN), N-methanesulfonyl-1,2-diphenylethylenediamine (MsDPEN), N-methyl-N'-(p-toluenesulfonyl)-1,2-diphenylethylenediamine, N-(p-methoxyphenylsulfonyl)-1,2-diphenylethylenediamine, N-(p-chlorophenylsulfonyl)-1,2-diphenylethylenediamine, N-trifluoromethanesulfonyl-1,2-diphenylethylenediamine, N-(2,4,6-trimethylbenzenesulfonyl)-1,2-diphenylethylenediamine, N-(2,4,6-triisopropylbenzenesulfonyl)-1,2-diphenylethylenediamine, N-(4-tert-butylbenzenesulfonyl)-1,2-diphenylethylenediamine, N-(2-naphthylsulfonyl)-1,2-diphenylethylenediamine, N-(3,5-dimethylbenzenesulfonyl)-1,2-diphenylethylenediamine, N-pentamethylbenzenesulfonyl-1,2-diphenylethylenediamine, and 1,2-N-tosylcyclohexanediamine (TsCYDN). Among these groups, TsDPEN and TsCYDN are preferred.

The sulfonate catalyst represented by the general formula (1) can be prepared by reaction of a metal amide complex with sulfonic acid such as trifluoromethanesulfonic acid. The sulfonate catalyst can also be prepared by reaction of a metal amide complex with a metal sulfonate such as ytterbium sulfonate. Further, the catalyst can be prepared by reaction of sulfonic acid such as trifluoromethanesulfonic acid with a metal amine complex having a ligand $X^2$ ($X^2$ an anionic group, for example, a hydride group, a hydroxyl group, a crosslinked oxo group, a fluorine group, a chlorine group, a bromine, or an iodine group) bonded to a metal. Further, the catalyst can be prepared by reaction of a metal amine complex having a ligand $X^2$ bonded to a metal with a metal sulfonate such as ytterbium sulfonate. When the amine complex is used as a starting material, the reaction may be sufficiently advanced by adding a base.

Methods for preparing the metal amide complex and the metal amine complex having an amine ligand, which are used as a raw material, are described in Angew. Chem., Int. Ed. Engl. Vol. 36, p. 285 (1997) and J. Org. Chem. Vol. 64, p. 2186 (1999). Specifically, such a complex can be synthesized by reaction between a transition metal complex such as a ruthenium arene complex, a pentamethylcyclopentadienyl rhodium complex, or a pentamethylcyclopentadienyl iridium complex and a sulfonyldiamine ligand.

The method for producing an alcohol of the present invention is performed by introducing the sulfonate catalyst represented by the general formula (1) and a ketone compound in a solvent and hydrogenating the ketone compound by mixing in the presence of hydrogen. With respect to the amount of the catalyst used in the method, the molar ratio S/C (wherein S is the substrate, and C is the catalyst) of the ketone compound to the sulfonate catalyst is not particularly limited but may be in the range of 10 to 100,000 from the viewpoint of practicability and preferably in the range of 50 to 10,000.

Examples of the solvent for the hydrogenation reaction include alcohol solvents, such as methanol, ethanol, 2-propanol, 2-methyl-2-propanol, and 2-methyl-2-butanol; ether solvents, such as tetrahydrofuran (THF) and diethyl ether; hetero atom-containing solvents, such as DMSO, DMF, and acetonitrile; aromatic hydrocarbon solvents, such as toluene and xylene; aliphatic hydrocarbon solvents, such as pentane and hexane; halogen-containing hydrocarbon solvents, such as methylene chloride; and water. These solvents can be used alone or in combination of two or more. Also, a mixed solvent containing any one of the above-exemplified solvents and another solvent can be used. Among these solvents, the alcohol solvents are preferred for efficiently advancing the reaction, and methanol and ethanol are more preferred. The amount of the solvent is determined from the viewpoint of solubility of the reaction substrate and economy. For example, when methanol is used, the hydrogenation reaction can be performed at a low concentration of 1% by weight or less to a high concentration of 99% by weight or more which is substantially close to a solvent-less state, and preferably at a concentration of 5 to 80% by weight. There has been known substantially no example in which hydrogenation reaction proceeds with high reactivity at such a high concentration. Such a method is extremely industrially useful because the production per batch of the hydrogenation reaction can be improved.

The hydrogen pressure is not particularly limited but may be in the range of 1 to 200 atm and preferably in the range of 5 to 150 atm in view of economy. The reaction temperature is particularly limited but may be in the range of −50° C. to 100° C., preferably in the range of −30° C. to 60° C., and more preferably in the range of 20° C. to 60° C. The reaction time depends on the type and concentration of the reaction substrate, the S/C ratio, the reaction conditions such as the temperature and pressure, and the type of the catalyst. Therefore, the conditions may be determined so that the reaction is terminated after several minutes to several days. In particular, the conditions are preferably determined so that the reaction is terminated after 5 to 24 hours. In addition, the reaction product can be arbitrarily purified by a known method such as column chromatography, distillation, or recrystallization.

In the method for producing an alcohol compound of the present invention, it is not essential to add a base to the reaction system, and thus the hydrogenation reaction of the ketone compound rapidly proceeds without addition of the base. However, the addition of the base is not excluded, and the base may be added in a small amount depending on, for example, the structure of the reaction substrate and the purity of the reagent used.

In the sulfonate complex represented by the general formula (1) of the present invention, both the chiral carbons at the two positions must be an (R)- or (S)-form in order to obtain an optically active alcohol. By selecting either the (R)- or (S)-form, an optically active alcohol with a desired absolute configuration can be highly selectively obtained. When a racemic alcohol or chiral alcohol is desired to be produced, it is not necessary that both chiral carbons are either the (R)- or (S)-form, and each of the carbons may be independently either the (R)- or (S)-form.

As described above, in the method for producing an alcohol compound of the present invention, the ketone compound is hydrogenated without the addition of the base, and thus the ketone compound unstable to the base can be hydrogenated to obtain a corresponding alcohol compound. Therefore, the method for producing an alcohol compound of the present invention can be applied to ketone compounds with a wide range of structures as compared with a conventional known method using a hydrogenation catalyst without using a base. Thus, the hydrogenation reaction is little affected by the influence of impurities and proceeds with high reproducibility, and a target substance can be obtained with high optical purity and high yield. Further, the sulfonate catalyst of the present invention is capable of producing an optically active cyclic alcohol by hydrogenation of a cyclic ketone which could have been not efficiently reduced with a hydrogenation catalyst, producing an optically active alcohol having an olefin portion or acetylene portion by hydrogenation of a ketone (particularly, a conjugated ketone having with an olefin or acetylene group) having an olefin or acetylene portion, producing an optically active alcohol having a hydroxyl group by hydrogenation of a ketone having a hydroxyl group, an optically active alcohol having a halogen substituent by hydrogenation of a ketone having a halogen substituent (particularly a ketone having a halogen substituent at an α-position), producing an optically active alcohol by hydrogenation of a cyclic ketone such as a chromanone derivative, producing an optically active diol by hydrogenation of a diketone, producing an optically active hydroxyester by hydrogenation of a ketoester, and producing an optically active hydroxyamide by hydrogenation of a ketoamide. Therefore, the method is extremely useful. Typical examples of ketone compounds which can be applied to the method for producing an optically active alcohol of the present invention are given below.

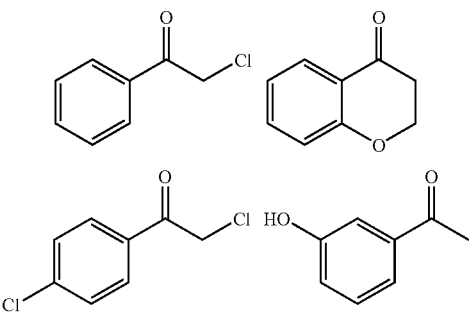

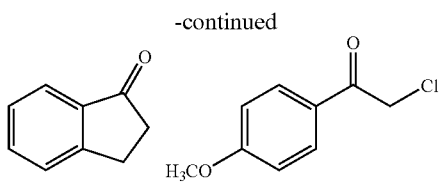

In the method for producing an alcohol compound of the present invention, when a ketone compound including an oxygen functional group or a cyano group near a carbonyl carbon (e.g., the α- or β-position), such as hydroxyketone, ketoester, or cyanoketone, is used as the reaction substrate, an iridium catalyst is preferably used because the iridium catalyst exhibits extremely high catalytic performance as compared with a ruthenium catalyst.

EXAMPLES

The present invention will be described in further detail below with reference to examples. Of course, the present invention is not limited to these examples, and the hydrogenation reaction of a ketone compound can be performed in either a batch reaction system or a continuous reaction system.

In the examples below, a solvent after drying and degassing was used in the reaction. In addition, NMR was measured using JNM-LA400 (400 MHz, manufactured by JEOL. Ltd.) and JNM-LA500 (500 MHz, manufactured by JEOL. Ltd.). $^1$HNMR and $^{13}$CNMR were measured using tetramethylsilane (TMS) as an internal standard whose signal was considered as δ=0 (δ is a chemical shift). The optical purity was measured by gas chromatography (GC) or high performance liquid chromatography (HPLC). GC was measured using Chirasil-DEX CB (0.25 mm×25 m, DF=0.25 μm) (manufactured by CHROMPACK), and HPLC was measured using CHIRALCEL OD (0.46 cm×25 cm), CHIRALCEL OB (0.46 cm×25 cm), or CHIRALCEL OJ-H (0.46 cm×25 cm) (manufactured by Daicel Chemical Industries, Ltd.). The specific rotatory power was measured using DIP-370 (manufactured by Nihon-Bunkou Co., Ltd.).

Example 1

Preparation of Ru(OTf)[(S,S)-Tsdpen](p-cymene) as Sulfonate Complex

First, Ru[(S,S)-Tsdpen](p-cymene) (200 mg, 0.34 mmol), TfOH (30 μl, 0.34 mmol) (manufactured by Kanto Chemical Co., Ltd.), and 3 ml of THF were charged in a 20 ml Schlenk-type reaction tube purged with argon. Then, the resultant mixture was stirred at room temperature for 1 hour. The produced precipitate was filtered off, washed with 5 ml of THF, and dried under reduced pressure (1 mmHg) to obtain 200 mg of Ru(OTf)[(S,S)-Tsdpen] (p-cymene). The spectral data of the resultant sulfonate complex was as follows:

$^1$HNMR (400 MHz, THF-d8) δ 1.37, 1.43 (each d, J=7 Hz, 3H, CH(C$\underline{H}_3$)$_2$), 2.18 (s, 3H, C$\underline{H}_3$), 2.29 (s, 3H, CH$_3$), 2.98 (m, 1H, C$\underline{H}$(CH$_3$)$_2$), 3.55 (m, 1$\overline{H}$, C$\underline{H}$NH), 3.85 (br.dd, J=11 Hz, 12 Hz, 1H, CHN$\underline{H}\underline{H}$), 3.94 (d, J=11 Hz, 1H, C$\underline{H}$NTs), 5.78 (d, J=6 Hz, 1H, aromatic H), 5.92-5.93 (m, 2H, aromatic H), 6.15 (d, J=6 Hz, 1H, aromatic H), 6.53-7.13 (m, 14H, aromatic H), 7.16 (br.d, 1H, CHN$\underline{H}$); $^{13}$CNMR (100.4 MHz, THF-d8) δ 18.6, 21.1, 22.6, 22.8, 31.4, 70.3, 73.2, 82.4, 82.9, 84.2, 84.3, 97.0, 101.2, 127.0, 127.8, 128.1, 128.6, 128.7, 128.8, 129.2, 130.0, 139.7, 139.9, 140.3, 143.6.

Ru[(S,S)-Tsdpen] (p-cymene) was synthesized according to the method described in the above-mentioned known document. The specific procedures are described below. First, [RuCl$_2$(p-cymene)]$_2$ (310 mg, 0.5 mmol) (manufactured by Kanto Chemical Co., Ltd.), (S,S)-TsDPEN (370 mg, 1 mmol), KOH (400 mg, 7 mmol), and 7 ml of methylene chloride were charged in a Schlenk-type reaction tube purged with argon. Then, the resultant mixture was stirred at room temperature for 5 minutes. Then, 7 ml of water was added to the mixture, followed by stirring at room temperature for 5 minutes. Then, the resulting layers were separated, and the methylene chloride layer was washed with 7 ml of water, and CaH$_2$ was added to the layer. After the mixture was dried, CaH$_2$ was removed by filtration, and methylene chloride was distilled off under reduced pressure (1 mmHg). The residue was dried to obtain 520 mg of Ru[(S,S)-Tsdpen](p-cymene).

Example 2

Preparation of Ru(OTf)[(S,S)-Tsdpen](p-cymene) as Sulfonate Complex

First, Ru[(S,S)-Tsdpen](p-cymene) (180 mg, 0.3 mmol), Yb(OTf)$_3$ (183 mg, 0.3 mmol) (manufactured by Aldrich), and 3 ml of CH$_3$OH were charged in a 20 ml Schlenk-type reaction tube purged with argon. Then, the resultant mixture was degassed and stirred at room temperature for 10 minutes. After CH$_3$OH was distilled off under reduced pressure (1 mm Hg), 2 ml of THF was added to the residue, and the produced precipitate was filtered off, washed with 1 ml of THF and with 5 ml of toluene, and dried under reduced pressure (1 mmHg) to obtain 130 mg of Ru(OTf)[(S,S)-Tsdpen](p-cymene).

Example 3

Preparation of Ru(OTf)[(R,R)-Tsdpen](mesitylene) as Sulfonate Complex

First, RuCl[(R,R)-Tsdpen](mesitylene) (210 mg, 0.34 mmol), KOH (27 mg, 0.48 mmol), 6 ml of methylene chloride, and 1 ml of water were charged in a 20 ml Schlenk-type reaction tube purged with argon. Then, the resultant mixture was stirred at room temperature for 10 minutes. After Na$_2$SO$_4$ was added to the reaction solution, the mixture was dried, and Na$_2$SO$_4$ was removed by filtration. Then, CaH was added to the filtrate, followed by stirring at room temperature for 30 minutes. After CaH was removed by filtration, the solvent was distilled off under reduced pressure (1 mm Hg), and 6 ml of THF and TfOH (30 μl, 0.34 mmol) (manufactured by Kanto Chemical Co., Ltd.) were added to the residue, followed by stirring at room temperature for 20 minutes. The produced precipitate was filtered off, washed with 2 ml of THF, and dried under reduced pressure (1 mmHg) to obtain 140 mg of Ru(OTf)[(R,R)-Tsdpen](mesitylene). The spectral data of the resultant sulfonate complex was as follows:

$^1$HNMR (400 MHz, CD$_3$OD) δ 2.22 (s, 3H, C$\underline{H}_3$), 2.38 (s, 9H, C$\underline{H}_3$), 3.74 (d, J=11 Hz, 1H, C$\underline{H}$NH$_2$), 4.06 $\overline{(d}$, J=11 Hz, 1H, C$\underline{H}$NTs), 5.74 (s, 3H, aromatic H), 6.63-7.18 (m, 14H, aromatic H)

RuCl[(R,R)-Tsdpen](mesitylene) was synthesized according to the method described in the above-mentioned known document. The specific procedures are described below. First, [RuCl$_2$(mesitylene)]$_2$ (1.5 g, 2.5 mmol), (R,R)-TsDPEN (1.8 g, 5 mmol), triethylamine (1.4 ml, 10 mmol), and 30 ml of 2-propanol were charged in a Schlenk-type reaction tube purged with argon. Then, the resultant mixture was stirred at 80° C. for 1 hour and concentrated under reduced pressure (1 mmHg). The precipitated crystal was filtered off, washed with 5 ml of water, and dried under reduced pressure (1 mmHg) to obtain 3 g of RuCl[(R,R)-Tsdpen](mesitylene).

Example 4

Preparation of Ru [OSO$_2$ (p-NO$_2$Ph)][(S,S)-Tsdpen] (p-cymene) as Sulfonate Complex First, Ru[(S,S)-Tsdpen](p-cymene) (251 mg, 0.42 mmol), (p-NO$_2$Ph)SO$_3$H (100 mg, 0.42 mmol) (manufactured by ACROS), and 4 ml of THF were charged in a 20 ml Schlenk-type reaction tube purged with argon. Then, the resultant mixture was stirred at room temperature for 2 hours. After THF was distilled off under reduced pressure (1 mmHg), 15 ml of toluene was added to the residue, and the produced precipitate was filtered off, washed with 10 ml of toluene, and dried under reduced pressure (1 mmHg) to obtain 230 mg of Ru(OSO$_2$(p-NO$_2$Ph))[(S,S)-Tsdpen](p-cymene). The spectral data of the resultant sulfonate complex was as follows:

$^1$HNMR (400 MHz, CD$_3$OD) δ 1.39, 1.43 (each d, J=7 Hz, 3H, CH(CH$_3$)$_2$), 2.23 (s, 3H, CH$_3$), 2.36 (s, 3H, CH$_3$), 3.02 (m, 1H, CH(CH$_3$)$_2$), 3.65 (d, J=11 Hz, 1H, CHNH$_2$), 4.00 (d, J=11 Hz, 1H, CHNTs), 5.68 (d, J=6 Hz, 1H, aromatic H), 6.03-6.07 (m, 3H, aromatic H), 6.58-7.17 (m, 14H, aromatic H), 8.00 (d, J=9 Hz, 2H, aromatic H), 8.26 (d, J=9 Hz, 2H, aromatic H).

Example 5

Preparation of Ru(OSO$_2$CH$_3$) [(S,S)-Tsdpen](p-cymene) as Sulfonate Complex

First, Ru[(S,S)-Tsdpen](p-cymene) (180 mg, 0.3 mmol), CH$_3$SO$_3$H (20 μl, 0.3 mmol) (manufactured by Kanto Chemical Co., Ltd.), and 3 ml of THF were charged in a 20 ml Schlenk-type reaction tube purged with argon. Then, the resultant mixture was stirred at room temperature for 1 hour. After THF was distilled off under reduced pressure (1 mmHg), 5 ml of toluene was added to the residue. The resultant mixture was concentrated to a total of 2 ml under reduced pressure (1 mmHg), and the produced precipitate was filtered off, washed with 2 ml of toluene, and dried under reduced pressure (1 mmHg) to obtain 130 mg of Ru(OSO$_2$CH$_3$) [(S,S)-Tsdpen](p-cymene). The spectral data of the resultant sulfonate complex was as follows:

$^1$HNMR (400 MHz, CD$_3$OD) δ 1.39, 1.43 (each d, J=7 Hz, 3H, CH(CH$_3$)$_2$), 2.24 (s, 3H, CH$_3$), 2.35 (s, 3H, CH$_3$), 2.70 (s, 3H, CH$_3$), 3.02 (m, 1H, CH(CH$_3$)$_2$), 3.62 (d, J=11 Hz, 1H, CHNH$_2$), 3.99 (d, J=11 Hz, 1H, CHNTs), 5.68 (d, J=6 Hz, 1H, aromatic H), 6.01-6.04 (m, 3H, aromatic H), 6.59-7.18 (m, 14H, aromatic H).

Example 6

Preparation of Cp*Ir(OTf)[(S,S)-Tsdpen] as Sulfonate Complex

First, Cp*Ir[(S,S)-Tsdpen] (78 mg, 0.11 mmol), TfOH 10 μl, 0.11 mmol) (manufactured by Kanto Chemical Co., Ltd.), and 5 ml of THF were charged in a 20 ml Schlenk-type reaction tube purged with argon. Then, the resultant mixture was stirred at room temperature for 1 hour. After THF was distilled off under reduced pressure (1 mmHg), the residue was dried to obtain 93 mg of Cp*Ir(OTf)[(S,S)-Tsdpen]. The spectral data of the resultant sulfonate complex was as follows:

$^1$HNMR (400 MHz, CD$_3$OD) δ 1.94 (s, 15H, CH$_3$), 2.29 (s, 3H, CH$_3$), 4.25 (br, 1H, CHNH$_2$), 4.65 (br, 1H, CHNTs), 6.92-7.39 (m, 14H, aromatic H).

Cp*Ir[(S,S)-Tsdpen] was synthesized according to the method described in the above-mentioned known document. The specific procedures are described below. First, [Cp*IrCl$_2$]$_2$ (660 mg, 1 mmol) (manufactured by Aldrich), (S,S)-TsDPEN (800 mg, 2.2 mmol), triethylamine (0.6 ml, 4.2 mmol), and 30 ml of 2-propanol were charged in a Schlenk-type reaction tube purged with argon. Then, the resultant mixture was stirred at room temperature for 12 hours and concentrated to 10 ml under reduced pressure (1 mmHg). The precipitated crystal was filtered off, washed with 5 ml of 2-propanol, and dried under reduced pressure (1 mmHg) to obtain 1.2 g of Cp*IrCl[(S,S)-Tsdpen]. Then, Cp*IrCl[(S,S)-Tsdpen] (21 mg, 0.032 mmol), 0.1M NaOHaq (32 μl, 0.032 mmol), and 5 ml of methylene chloride were charged in a Schlenk-type reaction tube purged with argon. Then, the resultant mixture was stirred at room temperature for 3 hours, and the solvent was distilled off under reduced pressure (1 mmHg), followed by drying to obtain 22 mg of Cp*Ir[(S,S)-Tsdpen].

Example 7

Synthesis of (R)-2-chloro-1-phenylethanol by Hydrogenation Reaction of α-Chloroacetophenone In a stainless steel autoclave, Ru(OTf) [(S,S)-Tsdpen] (p-cymene) (2.4 mg, 3.3 μmol) and α-chloroacetophenone (0.3 g, 2 mmol) were charged, followed by purging with argon. Then, 4 ml of methanol was added, and the autoclave was pressurized with hydrogen, followed by ten times of purging. Then, hydrogen was charged to 20 atm to initiate reaction. After stirring at 30° C. for 15 hours, the reaction pressure was returned to normal pressure. $^1$HNMR and GC analysis of the product showed that (R)-2-chloro-1-phenylethanol with 95% ee was produced in a yield of 100%. The spectral data of the resultant alcohol compound was as follows:

$^1$HNMR (400 MHz, CDCl$_3$) δ 2.61 (d, J=3 Hz, 1H, CHO H), 3.65 (dd, J=9 Hz, 11 Hz, 1H, CHHCl), 3.75 (dd, J=3 Hz, 11 Hz, 1H, CHHCl), 4.91 (ddd, J=3 Hz, 3 Hz, 9 Hz, 1H, CHOH), 7.27-7.39 (m, 5H, aromatic H); GC (Chirasil-DEX CB; column temperature, 130° C.; injection temperature, 250° C.; detection temperature, 275° C.; helium pressure, 100 kPa); $t_R$ of (R)-2-chloro-1-phenyl ethanol, 17.0 minutes; $t_R$ of (S)-2-chloro-1-phenylethanol, 15.7 minutes; $t_R$ of α-chloroacetophenone, 9.0 minutes; specific rotatory power $[α]^{20}{}_D$ –460 (c2.8, C$_6$H$_{12}$); document value, $[α]^{20}{}_D$ –48° (c2.8, C$_6$H$_{12}$), (R), Aldrich.

Examples 8 and 9

(R)-2-chloro-1-phenylethanol was synthesized by reaction under the same conditions as in Example 7 except that the substrate/catalyst ratio, the hydrogen pressure, and the type of the solvent were changed. The results are summarized in Table 1.

TABLE 1

$$\text{Ph-C(O)-CH}_2\text{Cl} + \text{H}_2 \xrightarrow[\text{solvent}]{\text{Ru catalyst}} \text{Ph-CH(OH)-CH}_2\text{Cl}$$

| Example | S/C | H₂ (atm) | ketone/solvent | solvent | yield (%) | ee (%) |
|---|---|---|---|---|---|---|
| 8 | 600 | 20 | 0.3 g/4 ml | CH₃CH₂OH | 100 | 95 |
| 9 | 1800 | 100 | 0.9 g/12 ml | CH₃OH/H₂O = 99/1 | 74 | 93 |

Conditions: Ru cat 3.3 mmol, temp 30° C., time 15 h.

Examples 10 to 14

(R)-2-chloro-1-phenylethanol was synthesized by reaction under the same conditions as in Example 7 except that the hydrogen pressure, the substrate/catalyst ratio, and the substrate concentration were changed. The results are summarized in Table 2. Example 14 showed that the hydrogenation reaction proceeds even at such a high substrate concentration that the substrate is not completely dissolved.

TABLE 2

$$\text{Ph-C(O)-CH}_2\text{Cl} + \text{H}_2 \xrightarrow[\text{methanol}]{\text{Ru catalyst}} \text{Ph-CH(OH)-CH}_2\text{Cl}$$

| Example | S/C | ketone/CH₃OH | yield (%) | ee (%) |
|---|---|---|---|---|
| 10 | 1800 | 0.9 g/3 ml | 100 | 95 |
| 11 | 1800 | 0.9 g/1.5 ml | 100 | 95 |
| 12 | 1800 | 0.9 g/0.8 ml | 100 | 94 |
| 13 | 3000 | 1.5 g/1.3 ml | 100 | 94 |
| 14 | 6100 | 3 g/0.7 ml$^a$ | 68 | 92 |

Conditions: Ru cat 3.3 mmol, H₂ 100 atm, temp 30° C., time 15 h.
$^a$Substrate was not completely dissolved.

Example 15

Synthesis of (S)-4-chromanol by Hydrogenation Reaction of 4-chromanone

In a stainless steel autoclave, Ru(OTf)[(S,S)-Tsdpen](p-cymene) (2.4 mg, 3.3 μmol) and 4-chromanone (1.48 g, 10 mmol) were charged, followed by purging with argon. Then, 0.5 ml of methanol was added, and the autoclave was pressurized with hydrogen, followed by ten times of purging. Then, hydrogen was charged to 15 atm to initiate reaction. After stirring at 50° C. for 15 hours, the reaction pressure was returned to normal pressure. ¹HNMR and HPLC analysis of the product showed that (S)-4-chromanol with 91% ee was produced in a yield of 100%. The spectral data of the resultant alcohol compound was as follows: ¹HNMR (400 MHz, CDCl₃) δ 1.99 (m, 1H, CH̲HCHOH), 2.08 (m, 1H, CH HCHOH), 2.31 (br, 1H, OH), 4.23 (m, 2H, CH₂OC), 4.74 (m, 1H, CH̲OH), 6.81-6.92 (m, 2H, aromatic H), 7.17-7.30 (m, 2H, aromatic H); HPLC (CHIRALCEL OJ-H; solvent, hexane/2-propanol=99/1; flow rate, 1.5 ml/min; temperature, 35°; UV wavelength, 220 nm); $t_R$ of (S)-4-chromanol, 26.7 minutes; $t_R$ of (R)-4-chromanol, 30.8 minutes; $t_R$ of 4-chromanone, 11.8 minutes; specific rotatory power $[\alpha]^{25}_D$ −72° (c0.5, C₂H₅OH); document value, $[\alpha]^{25}_D$ +80.4° (c0.5, C₂H₅OH), 100% ee (R), J. Am. Chem. Soc., 1993, 115, 3318.

Comparative Example 1

In a stainless steel autoclave, Ru[(S,S)-Tsdpen](p-cymene) (1.2 mg, 2 μmol) and 4-chromanone (0.3 g, 2 mmol) were charged, followed by purging with argon. Then, 2 ml of methanol was added, and the autoclave was pressurized with hydrogen, followed by ten times of purging. Then, hydrogen was charged to 30 atm to initiate reaction. After stirring at 50° C. for 15 hours, the reaction pressure was returned to normal pressure. ¹HNMR and HPLC analysis of the product showed that (S)-4-chromanol with 86% ee was produced in a yield of 7%. As a result, it was found that the sulfonate catalyst of the present invention exhibits excellent activity as compared with a conventional well-known ruthenium complex.

Example 16

Synthesis of (S)-4-chromanol by Hydrogenation Reaction of 4-chromanone

In a stainless steel autoclave, Ru(OTf)[(S,S)-Tsdpen](p-cymene) (2.4 mg, 3.3 μmol) and 4-chromanone (1.48 g, 10 mmol) were charged, followed by purging with argon. Then, 0.7 ml of methanol was added, and the autoclave was pressurized with hydrogen, followed by ten times of purging. Then, hydrogen was charged to 15 atm to initiate reaction. After stirring at 50° C. for 15 hours, the reaction pressure was returned to normal pressure. ¹HNMR and HPLC analysis of the product showed that (S)-4-chromanol with 93% ee was produced in a yield of 100%.

Example 17

Synthesis of (S)-4-chromanol by Hydrogenation Reaction of 4-chromanone

In a stainless steel autoclave, Ru(OTf)[(S,S)-Tsdpen](p-cymene) (2.4 mg, 3.3 μmol), Yb(OTf)₃ (0.62 mg, 1 μmol), and 4-chromanone (1.48 g, 10 mmol) were charged, followed by purging with argon. Then, 0.7 ml of methanol was added, and the autoclave was pressurized with hydrogen, followed by ten times of purging. Then, hydrogen was charged to 15 atm to initiate reaction. After stirring at 50° C. for 15 hours, the reaction pressure was returned to normal pressure. $^1$HNMR and HPLC analysis of the product showed that (S)-4-chromanol with 97% ee was produced in a yield of 98%.

Examples 18 to 20

(S)-4-chromanol was synthesized by reaction under the same conditions as in Example 15 except that the substrate/catalyst ratio and the hydrogen pressure were changed. The results are summarized in Table 3.

TABLE 3

| Example | S/C | ketone/CH$_3$OH | yield (%) | ee (%) |
|---|---|---|---|---|
| 18 | 4900 | 2.4 g/0.8 ml | 100 | 92 |
| 19 | 8000 | 3.9 g/1.3 ml | 100 | 92 |
| 20 | 9800 | 4.7 g/1.6 ml | 95 | 92 |

Conditions: Ru cat 3.3 mmol, H$_2$ 100 atm, temp 50° C., time 15 h

Example 21

Synthesis of (R)-4-chromanol by Hydrogenation Reaction of 4-chromanone

In a stainless steel autoclave, Ru(OTf)[(R,R)-Tsdpen](p-cymene) (2.4 mg, 3.3 μmol) and 4-chromanone (1.48 g, 10 mmol) were charged, followed by purging with argon. Then, 0.5 ml of methanol was added, and the autoclave was pressurized with hydrogen, followed by ten times of purging. Then, hydrogen was charged to 15 atm to initiate reaction. After stirring at 50° C. for 15 hours, the reaction pressure was returned to normal pressure. $^1$HNMR and HPLC analysis of the product showed that (R)-4-chromanol with 83% ee was produced in a yield of 54%.

Example 22

Synthesis of (S)-4-chromanol by Hydrogenation Reaction of 4-chromanone

In a stainless steel autoclave, Ru[OSO$_2$(p-NO$_2$Ph)][(S,S)-Tsdpen](p-cymene) (2.6 mg, 3.3 μmol) and 4-chromanone (1.48 g, 10 mmol) were charged, followed by purging with argon. Then, 0.5 ml of methanol was added, and the autoclave was pressurized with hydrogen, followed by ten times of purging. Then, hydrogen was charged to 15 atm to initiate reaction. After stirring at 50° C. for 15 hours, the reaction pressure was returned to normal pressure. $^1$HNMR and HPLC analysis of the product showed that (S)-4-chromanol with 91% ee was produced in a yield of 77%.

Example 23

Synthesis of (S)-4-chromanol by Hydrogenation Reaction of 4-chromanone

In a stainless steel autoclave, Ru(OSO$_2$CH$_3$) [(S,S)-Tsdpen] (p-cymene) (1.4 mg, 2 μmol) and 4-chromanone (300 mg, 2 mmol) were charged, followed by purging with argon. Then, 0.1 ml of methanol was added, and the autoclave was pressurized with hydrogen, followed by ten times of purging. Then, hydrogen was charged to 15 atm to initiate reaction. After stirring at 50° C. for 15 hours, the reaction pressure was returned to normal pressure. $^1$HNMR and HPLC analysis of the product showed that (S)-4-chromanol with 95% ee was produced in a yield of 98%.

Example 24

Synthesis of (S)-4-chromanol by Hydrogenation Reaction of 4-chromanone

In a stainless steel autoclave, Cp*Ir(OTf)[(S,S)-Tsdpen] (1.6 mg, 2 μmol) and 4-chromanone (300 mg, 2 mmol) were charged, followed by purging with argon. Then, 0.4 ml of methanol was added, and the autoclave was pressurized with hydrogen, followed by ten times of purging. Then, hydrogen was charged to 30 atm to initiate reaction. After stirring at 50° C. for 15 hours, the reaction pressure was returned to normal pressure. $^1$HNMR and HPLC analysis of the product showed that (S)-4-chromanol with 95% ee was produced in a yield of 95%.

Example 25

Synthesis of 2-chloro-1-(p-chlorophenyl)ethanol by Hydrogenation Reaction of 2,4'-dichloroacetophenone In a stainless steel autoclave, Ru(OTf)[(S,S)-Tsdpen](p-cymene) (2.4 mg, 3.3 μmol) and 2,4'-dichloroacetophenone (1.1 g, 6 mmol) were charged, followed by purging with argon. Then, 0.75 ml of methanol was added, and the autoclave was pressurized with hydrogen, followed by ten times of purging. Then, hydrogen was charged to 100 atm to initiate reaction. After stirring at 30° C. for 15 hours, the reaction pressure was returned to normal pressure. $^1$HNMR and GC analysis of the product showed that 2-chloro-1-(p-chlorophenyl)ethanol with 92% ee was produced in a yield of 100%. The spectral data of the resultant alcohol compound was as follows:

$^1$HNMR (400 MHz, CDCl$_3$) δ 2.88 (br, 1H, OH), 3.58 (m, 1H, CHHCHOH), 3.68 (m, 1H, CHHCHOH), 4.85 (m, 1H, CHOH), 7.26 (m, 4H, aromatic H); GC (Chirasil-DEX CB; column temperature, 140° C.; injection temperature, 250° C.; detection temperature, 275° C.; helium pressure, 100 kPa); t$_R$ of optical isomers of 2-chloro-1-(p-chlorophenyl)ethanol, 31.4 minutes and 34.7 minutes; R and S isomers, not identified.

Example 26

Synthesis of 1-(m-hydroxyphenyl)ethanol by Hydrogenation Reaction of m-hydroxyacetophenone In a stainless steel autoclave, Ru(OTf)[(S,S)-Tsdpen](p-cymene) (2.4 mg, 3.3 μmol) and m-hydroxyacetophenone (1.1 g, 8 mmol) were charged, followed by purging with argon. Then, 1 ml of methanol was added, and the autoclave was pressurized with hydrogen, followed by ten times of purging. Then, hydrogen was charged to 100 atm to initiate reaction. After stirring at 30° C. for 15 hours, the reaction pressure was returned to normal pressure. $^1$HNMR and HPLC analysis of the product showed that 1-(m-hydroxyphenyl)ethanol with 94% ee was produced in a yield of 100%. The spectral data of the resultant alcohol compound was as follows:

$^1$HNMR (400 MHz, acetone-d6) δ 1.37 (d, J=6 Hz, 3H, CH$_3$), 4.07 (d, J=4 Hz, 1H, CHOH), 4.77 (m, 1H, CHOH), 6.67-7.13 (m, 4H, aromatic H), 8.15 (s, 1H, OH); HPLC (CHIRALCEL OB; solvent, hexane/2-propanol=95/5; flow rate, 1.0 ml/min; temperature, 35° C.; UV wavelength, 254 nm); $t_R$ of optical isomers of 1-(m-hydroxyphenyl)ethanol, 17.2 minutes and 31.5 minutes; R and S isomers, not identified.

Example 27

Synthesis of 1-indanol by Hydrogenation Reaction of 1-indanone

In a stainless steel autoclave, Ru(OTf)[(S,S)-Tsdpen](p-cymene) (2.4 mg, 3.3 μmol) and 1-indanone (0.8 g, 6 mmol) were charged, followed by purging with argon. Then, 0.75 ml of methanol was added, and the autoclave was pressurized with hydrogen, followed by ten times of purging. Then, hydrogen was charged to 100 atm to initiate reaction. After stirring at 30° C. for 15 hours, the reaction pressure was returned to normal pressure. $^1$HNMR and HPLC analysis of the product showed that 1-indanol with 97% ee was produced in a yield of 95%. The spectral data of the resultant alcohol compound was as follows:

$^1$HNMR (400 MHz, CDCl$_3$) δ 1.92 (m, 1H, CHHC), 2.40 (s, 1H, OH), 2.45 (m, 1H, CHHC), 2.79 (m, 1H, CHHCHOH), 3.03 (m, 1H, CHHCHOH), 5.20 (m, 1H, CHOH), 7.20-7.40 (m, 4H, aromatic H); HPLC (CHIRALCEL OB-H; solvent, hexane/2-propanol=9/1; flow rate, 0.5 ml/min; temperature, 35° C.; UV wavelength, 254 nm); $t_R$ of optical isomers of 1-indanol, 10.9 minutes and 16.0 minutes; R and S isomers, not identified.

Example 28

Synthesis of 2-chloro-1-(p-methoxyphenyl)ethanol by Hydrogenation Reaction of 4-methoxyphenacyl Chloride In a stainless steel autoclave, Ru(OTf)[(S,S)-Tsdpen](p-cymene) (1.2 mg, 1.6 μmol) and 4-methoxyphenacyl chloride (1.1 g, 6 mmol) were charged, followed by purging with argon. Then, 0.75 ml of methanol was added, and the autoclave was pressurized with hydrogen, followed by ten times of purging. Then, hydrogen was charged to 100 atm to initiate reaction. After stirring at 30° C. for 15 hours, the reaction pressure was returned to normal pressure. $^1$HNMR and HPLC analysis of the product showed that 2-chloro-1-(p-methoxyphenyl)ethanol with 94% ee was produced in a yield of 73%. The spectral data of the resultant alcohol compound was as follows:

$^1$HNMR (400 MHz, CDCl$_3$) δ 3.36 (br, 1H, CHOH), 3.57-3.66 (m, 2H, CH$_2$CHOH), 3.76 (s, 3H, OCH$_3$), 4.80 (m, 1H, CHOH), 6.86 (d, J=9 Hz, 2H, aromatic H), 7.27 (d, J=9 Hz, 2H, aromatic H); GC (Chirasil-DEX CB; column temperature, 140° C.; injection temperature, 250° C.; detection temperature, 275° C.; helium pressure, 100 kPa); $t_R$ of optical isomers of 2-chloro-1-(p-methoxyphenyl)ethanol, 30.1 minutes and 31.7 minutes; R and S isomers, not identified.

Example 29

Preparation of Cp*Ir(OTf)[(S,S)-Msdpen] as Sulfonate Catalyst

First, Cp*Ir[(S,S)-Msdpen] (200 mg, 0.325 mmol) and 10 ml of methylene chloride were charged in a 20 ml Schlenk-type reaction tube purged with argon. Then, a solution of TfOH (26 μl, 0.295 mmol) (manufactured by Kanto Chemical Co., Ltd.) in 5 ml of methylene chloride was added dropwise to the resultant-mixture, followed by stirring at room temperature for 1 hour. After methylene chloride was distilled off under reduced pressure (1 mmHg), the residue was washed with a mixed solvent of toluene and hexane and dried to obtain 93 mg of Cp*Ir(OTf)[(S,S)-Msdpen]. The spectral data of the resultant sulfonate complex was as follows:

$^1$HNMR (400 MHz, CD$_3$OD) δ 1.89 (s, 15H, CH$_3$), 2.26 (s, 3H, CH$_3$) 4.37 (br, 1H, CHNH$_2$), 5.05 (br, 1H, CHNMs), 7.23-7.43 (m, 10H, aromatic H)

Cp*Ir[(S,S)-Msdpen] was synthesized according to the method described in the above-mentioned known document. The specific procedures are described below. First, [Cp*IrCl$_2$]$_2$ (500 mg, 0.63 mmol), (R,R)-TsDPEN (1.8 g, 5 mmol), triethylamine (1.4 ml, 10 mmol), (S,S)-MsDPEN (364 mg, 1.26 mmol), potassium hydroxide (manufactured by Kanto Chemical Co., Ltd. 86% content) (409 mg, 6.28 mmol), 12 ml of methylene chloride, and 12 ml of water were charged in a Schlenk-type reaction tube purged with argon. Then, the resultant mixture was stirred at room temperature for 1 hour, and an aqueous layer was removed with an injection cylinder. Then, 5 ml of water was added, and the resultant mixture was stirred and allowed to stand. Then, the aqueous layer was removed. After this operation was repeated 8 times, the solution was dried with sodium sulfate. The solution portion was separated and placed in another Schlenk flask, and the solvent was distilled off to obtain 696 mg of Cp*Ir[(S,S)-Msdpen].

Example 30

Synthesis of Optically Active 1-phenyl-1,2-ethanediol by Hydrogenation Reaction of α-hydroxyacetophenone In a stainless steel autoclave, Cp*Ir(OTf)[(S,S)-Tsdpen] (1.7 mg, 2.0 μmol) and α-hydroxyacetophenone (0.136 g, 1.0 mmol) were charged, followed by purging with argon. Then, 1 ml of methanol was added, and the autoclave was pressurized with hydrogen, followed by ten times of purging. Then, hydrogen was charged to 100 atm to initiate reaction. After stirring at 50° C. for 16 hours, the reaction pressure was returned to normal pressure. $^1$HNMR and HPLC analysis of the product showed that optically active 1-phenyl-1,2-ethanediol with 82% ee was produced in a yield of 100%. The spectral data of the resultant alcohol compound was as follows:

$^1$HNMR (400 MHz, CD$_3$COCD$_3$) δ 3.53 (dd, J=2 Hz, 4 Hz, 1H, CHHOH), 3.64 (dd, J=2 Hz, 10 Hz, 1H, CHHOH), 4.04 (br, H, OH), 4.43 (br, 1H, OH), 4.73 (dd, J=4 Hz, 10 Hz, 1H, CHOH), 7.21-7.40 (m, 5H, aromatic H); HPLC (CHIRALCEL OB; solvent, hexane/2-propanol=98/2; flow rate, 1.0 ml/min; temperature, 35° C.; UV wavelength, 220 nm); $t_R$ of both optical isomers of 1-phenyl-1,2-ethanediol, 26.0 minutes and 36.2 minutes. In the reaction, the optical isomer detected at 26.0 minutes was a main component, but R and S isomers were not identified.

The hydrogenation reaction of α-hydroxyacetophenone was performed by the same method as in Example 30 except that the sulfonate catalyst was changed to Ru(OTf)[(S,S)-Tsdpen] (p-cymene). As a result, 67% ee of optically active 1-phenyl-1,2-ethanediol was produced in a yield of only 3%.

Example 31

Synthesis of Optically Active
1-phenyl-1,2-ethanediol by Hydrogenation Reaction
of α-hydroxyacetophenone In a stainless steel autoclave, Cp*Ir(OTf)[(S,S)-Msdpen] (1.5 mg, 2.0 μmol) and α-hydroxyacetophenone (0.272 g, 2.0 mmol) were charged, followed by purging with argon. Then, 2 ml of methanol was added, and the autoclave was pressurized with hydrogen, followed by ten times of purging. Then, hydrogen was charged to 100 atm to initiate reaction. After stirring at 50° C. for 16 hours, the reaction pressure was returned to normal pressure. $^1$HNMR and HPLC analysis of the product showed that optically active 1-phenyl-1,2-ethanediol with 98% ee was produced in a yield of 100%. The R and S isomers were not identified.

Example 32

Synthesis of 1-phenyl-1,2-ethanediol by
Hydrogenation Reaction of α-hydroxyacetophenone The reaction of α-hydroxyacetophenone was performed by the same method as in Example 3 except that the reaction was performed at a hydrogen pressure of 10 atm. As a result, optically active 1-phenyl-1,2-ethanediol with 97% ee was produced in a yield of 98%. The R and S isomers were not identified.

Example 33

Synthesis of Optically Active
1-phenyl-1,2-ethanediol by Hydrogenation Reaction
of α-hydroxyacetophenone In a stainless steel autoclave, Cp*Ir(OTf)[(S,S)-Msdpen] (1.5 mg, 2.0 μmol) and α-hydroxyacetophenone (0.545 g, 40 mmol) were charged, followed by purging with argon. Then, 4 ml of methanol was added, and the autoclave was pressurized with hydrogen, followed by ten times of purging. Then, hydrogen was charged to 100 atm to initiate reaction. After stirring at 50° C. for 24 hours, the reaction pressure was returned to normal pressure. $^1$HNMR and HPLC analysis of the product showed that optically active 1-phenyl-1,2-ethanediol with 97% ee was produced in a yield of 100%. The R and S isomers were not identified.

Example 34

Synthesis of (R)-methyl Mandelate by
Hydrogenation Reaction of Methyl Benzoylformate In a stainless steel autoclave, Cp*Ir(OTf)[(S,S)-Tsdpen] (1.7 mg, 2.0 mmol) was charged, followed by purging with argon. Then, 1 ml of methanol and methyl benzoylformate (0.28 ml, 2.0 mmol) were charged, and the autoclave was pressurized with hydrogen, followed by ten times of purging. Then, hydrogen was charged to 30 atm to initiate reaction. After stirring at 50° C. for 15 hours, the reaction pressure was returned to normal pressure. $^1$HNMR and HPLC analysis of the product showed that (R)-methyl mandelate with 66% ee was quantitatively produced. The spectral data of the resultant alcohol compound was as follows:

$^1$HNMR (400 MHz, CDCl$_3$) δ 3.75 (s, 3H, CH$_3$), 5.18 (s, 1H, CHOH), 7.26-7.43 (m, 5H, aromatic H); HPLC (CHIRALCEL OJ-H; solvent, hexane/2-propanol=98/2; flow rate, 1.0 ml/min; temperature, 35° C.; UV wavelength, 254 nm); $t_R$ of (R)-methyl mandelate, 29.0 minutes, $t_R$ of (S)-methyl mandelate, 30.8 minutes.

Example 35

Synthesis of (R)-methyl Mandelate by
Hydrogenation Reaction of Methyl Benzoylformate The hydrogenation reaction of methyl benzoylformate was performed by the same method as in Example 34 except that Cp*Ir(OTf)[(S,S)-Msdpen] (1.5 mg, 2.0 μmol) was used as the catalyst. As a result, (R)-methyl mandelate with 44% ee was quantitatively produced.

Example 36

Synthesis of Optically Active Ethyl
3-hydroxy-3-phenylpropionate by Hydrogenation
Reaction of Ethyl Benzoylacetate In a stainless steel autoclave, Cp*Ir(OTf)[(S,S)-Tsdpen] (1.7 mg, 2.0 mmol) was charged, followed by purging with argon. Then, 1 ml of methanol and ethyl benzoylacetate (0.34 ml, 2.0 mmol) were charged, and the autoclave was pressurized with hydrogen, followed by ten times of purging. Then, hydrogen was charged to 30 atm to initiate reaction. After stirring at 50° C. for 15 hours, the reaction pressure was returned to normal pressure. $^1$HNMR and HPLC analysis of the product showed that optically active ethyl 3-hydroxy-3-phenylpropionate with 91% ee was produced in a yield of 36%. The spectral data of the resultant alcohol compound was as follows:

$^1$HNMR (400 MHz, CDCl$_3$) δ 1.27 (t, J=2 Hz, 3H, CH$_3$), 2.73 (m, 2H, CHH), 4.16 (m, 2H, CH$_2$CH$_3$), 5.12 (m, 1H, CHOH), 7.26-7.39 (m, 5H, aromatic H); HPLC (CHIRALCEL OD-H; solvent, hexane/2-propanol 99/1; flow rate, 1.0 ml/min; temperature, 35° C.; UV wavelength, 220 nm); $t_R$ of both optical isomers of ethyl 3-hydroxy-3-phenylpropionate, 34.2 minutes and 45.3 minutes. In the reaction, the optical isomer detected at 34.2 minutes was a main component, but R and S isomers were not identified.

Example 37

Synthesis of Optically Active Ethyl 3-hydroxy-3-phenylpropionate by Hydrogenation Reaction of Ethyl Benzoylacetate In a stainless steel autoclave, Cp*Ir(OTf)[(S,S)-Msdpen] (1.5 mg, 2.0 μmol) was charged, followed by purging with argon. Then, 0.5 ml of methanol and ethyl benzoylacetate (0.17 ml, 1.0 mmol) were charged, and the autoclave was pressurized with hydrogen, followed by ten times of purging. Then, hydrogen was charged to 30 atm to initiate reaction. After stirring at 50° C. for 15 hours, the reaction pressure was returned to normal pressure. $^1$HNMR and HPLC analysis of the product showed that optically active ethyl 3-hydroxy-3-phenylpropionate with 93% ee was produced in a yield of 92%. The R and S isomers were not identified.

Example 38

Synthesis of (S)-methyl Lactate by Hydrogenation Reaction of Methyl Pyruvate

In a stainless steel autoclave, Cp*Ir(OTf)[(S,S)-Tsdpen] (1.7 mg, 2.0 μmol) was charged, followed by purging with argon. Then, 1 ml of methanol and methyl pyruvate (0.18 ml, 2.0 mmol) were charged, and the autoclave was pressurized with hydrogen, followed by ten times of purging. Then, hydrogen was charged to 30 atm to initiate reaction. After stirring at 50° C. for 15 hours, the reaction pressure was returned to normal pressure. $^1$HNMR and GC analysis of the product showed that (S)-methyl lactate with 76% ee was quantitatively produced. The spectral data of the resultant alcohol compound was as follows:

$^1$HNMR (400 MHz, CDCl$_3$) δ 1.42 (d, J=7 Hz, 3H, C$\underline{H}_3$), 3.10 (br, 1H, O$\underline{H}$), 3.79 (s, 3H, OC$\underline{H}_3$), 4.30 (q, J=7 Hz, 1H, C$\underline{H}$OH); GC (Chirasil-DEX CB; column temperature, 80° C.; injection temperature, 250° C.; detection temperature, 275° C.; helium pressure, 100 kPa); t$_R$ of (R)-methyl lactate, 3.11 minutes; t$_R$ of (S)-methyl lactate, 3.49 minutes.

The hydrogenation reaction of methyl pyruvate was performed by the same method as in Example 38 except that the sulfonate catalyst was changed to Ru(OTf)[(S,S)-Tsdpen] (p-cymene). As a result, (S)-methyl lactate with 33% ee was produced in a yield of only 25%.

Example 39

Synthesis of (S)-methyl Lactate by Hydrogenation Reaction of Methyl Pyruvate

The hydrogenation reaction of methyl pyruvate was performed by the same method as in Example 10 except that Cp*Ir(OTf)[(S,S)-Msdpen] (1.5 mg, 2.0 μmol) was used. As a result, (S)-methyl lactate with 78% ee was quantitatively produced.

Example 40

Synthesis of Optically Active 1-[3',4'-bis(benzyloxy)phenyl]-2-chloroethanol by hydrogenation reaction of 3',4'-bis(benzyloxy)-2-chloroacetophenone In a stainless steel autoclave, Cp*Ir(OTf)[(S,S)-Tsdpen] (1.5 mg, 2.0 μmol) and 3',4'-bis(benzyloxy)-2-chloroacetophenone (0.367 g, 1.0 mmol) were charged, followed by purging with argon. Then, 1.1 ml of methanol and 0.36 ml of dimethylformamide were charged, and the autoclave was pressurized with hydrogen, followed by ten times of purging. Then, hydrogen was charged to 100 atm to initiate reaction. After stirring at 50° C. for 18 hours, the reaction pressure was returned to normal pressure. $^1$HNMR and HPLC analysis of the product showed that optically active 1-[3',4'-bis(benzyloxy)phenyl]-2-chloroethanol with 82% ee was produced in a yield of 100%. The spectral data of the resultant alcohol compound was as follows:

$^1$HNMR (400 MHz, CD$_3$Cl$_3$) δ 3.55 (dd, J=9 Hz, 11 Hz, 1H, C$\underline{H}$HCl), 3.64 (dd, J=3 Hz, 11 Hz, 1H, CH$\underline{H}$Cl), 4.78 (dd, J=3 Hz, 9 Hz, 1H, C$\underline{H}$OH), 5.15 (s, 2H, OC$\underline{H}_2$Ph), 5.16 (s, 2H, OC$\underline{H}_2$Ph), 6.86-7.45 (m, 13H, aromatic H). The optical purity of the resultant alcohol was measured by reaction with 4 N sodium hydroxide in 2-propanol at 0° C. for 1 hour to be converted to 1-[3',4'-bis(benzyloxy)phenyl]-ethane-1,2-oxide, and then HPLC analysis. HPLC (CHIRALCEL AS-H; solvent, hexane/2-propanol=98/2; flow rate, 0.5 ml/min; temperature, 35° C.; UV wavelength, 215 nm); t$_R$ of both optical isomers of 1-[3',4'-bis(benzyloxy)phenyl]-ethane-1,2-oxide, 26.2 minutes and 30.0 minutes. In the reaction, the optical isomer detected at 26.2 minutes was a main component, but R and S isomers were not identified.

Example 41

Synthesis of 2-cyano-1-phenylethanol by Hydrogenation Reaction of α-cyanoacetophenone In a stainless steel autoclave, Cp*Ir(OTf)[(S,S)-Msdpen] (1.5 mg, 2.0 μmol) and α-cyanoacetophenone (0.15 g, 1.0 mmol) were charged, followed by purging with argon. Then, 5 ml of methanol was charged, and the autoclave was pressurized with hydrogen, followed by ten times of purging. Then, hydrogen was charged to 30 atm to initiate reaction. After stirring at 50° C. for 15 hours, the reaction pressure was returned to normal pressure. $^1$HNMR and HPLC analysis of the product showed that optically active 2-cyano-1-phenylethanol with 96% ee was quantitatively produced. The spectral data of the resultant alcohol compound was as follows:

$^1$HNMR (400 MHz, CDCl$_3$) δ 2.51 (brs, 1H, O$\underline{H}$), 2.76 (m, 2H, C$\underline{H}$HCN), 5.04 (t, J=6.0 Hz, H, C$\underline{H}$OH), 7.35-7.50 (m, 5H, aromatic H); HPLC (CHIRALCEL OJ-H; solvent, hexane/2-propanol=95/5; flow rate, 1.0 ml/min; temperature, 35° C.; UV wavelength, 254 nm); t$_R$ of (S)-2-cyano-1-phenylethanol, 42.5 minutes; t$_R$ of (R)-2-cyano-1-phenylethanol, 47.7 minutes.

The hydrogenation reaction of α-cyanoacetophenone was performed by the same method as in Example 41 except that the sulfonate catalyst was changed to Ru(OTf)[(S,S)-Tsdpen] (p-cymene). As a result, the reaction did not proceed.

INDUSTRIAL APPLICABILITY

The present invention is used for producing optically active alcohols which are used as synthesis intermediates of medicines, agricultural chemicals, or many general-purpose chemicals.

The invention claimed is:

1. A sulfonate catalyst represented by general formula (1) and used for a hydrogenation reaction:

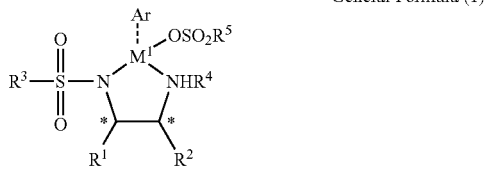

General Formula (1)

wherein
- $R^1$ and $R^2$ may be the same or different and each represent an alkyl group, a phenyl group, a naphthyl group, or a cycloalkyl group, which may be substituted, or a part of an alicyclic ring formed by bonding of $R^1$ and $R^2$;
- $R^3$ represents an alkyl group, a phenyl group, a naphthyl group, or camphor which may be substituted;
- $R^4$ represents a hydrogen atom or an alkyl group;
- $R^5$ represents an alkyl group, a phenyl group, a naphthyl group, or camphor which may be substituted;
- Ar is bonded to $M^1$ through a π bond and represents benzene which may be substituted or a cyclopentadienyl group which may be substituted;
- $M^1$ represents ruthenium, rhodium, or iridium; and
- * represents a chiral carbon.

2. The sulfonate catalyst according to claim 1, wherein in the general formula (I), $R^1$ and $R^2$ may be the same or different and each represent a phenyl group, a phenyl group containing one or more alkyl groups having 1 to 5 carbon atoms, a phenyl group containing one or more alkoxy groups having 1 to 5 carbon atoms, a phenyl group containing one or more halogen substituents, or an alkyl group which may form a 5- or 6-membered ring by bonding of $R^1$ and $R^2$.

3. The sulfonate catalyst according to claim 1, wherein $R^5$ in the general formula (I) is an alkyl group containing at least one fluorine atom.

4. A method for producing an alcohol compound comprising hydrogenating a ketone compound with the sulfonate catalyst according to claim 1 in the presence of hydrogen or a hydrogen-donating compound to produce an alcohol compound.

5. A method for producing an alcohol compound comprising hydrogenating a ketone compound with the sulfonate catalyst according to claim 1 in the presence of hydrogen or a hydrogen-donating compound to produce an optically active alcohol compound, wherein both chiral carbons at the two positions in the sulfonate catalyst are an (R)- or (S)-form.

6. The method according to claim 4, wherein the ketone compound is hydrogenated using as a solvent at least one selected from the group consisting of methanol, ethanol, and 2-propanol.

7. A method for producing an alcohol compound comprising hydrogenating a ketone compound which has an oxygen functional group or a cyano group near a carbonyl carbon with the sulfonate catalyst according to claim 1 in the presence of hydrogen or a hydrogen-donating compound to produce an alcohol compound, wherein $M^1$ the general formula (I) is iridium.

8. A method for producing an alcohol compound comprising hydrogenating a ketone compound which has an oxygen functional group or a cyano group near a carbonyl carbon with the sulfonate catalyst according to claim 1 in the presence of hydrogen or a hydrogen-donating compound to produce an optically active alcohol compound, wherein $M^1$ in the general formula (1) is iridium and both chiral carbons at the two positions in the sulfonate catalyst are an (R)- or (S)-form.

9. The method according to claim 7, wherein the ketone compound is α- or β-hydroxyketone, α- or β-ketoester, or α- or β-cyanoketone.

10. The method according to claim 5, wherein the ketone compound is hydrogenated using as a solvent at least one selected from the group consisting of methanol, ethanol, and 2-propanol.

11. The method according to claim 8, wherein the ketone compound is α- or β-hydroxyketone, α- or β-ketoester, or α- or β-cyanoketone.

12. A method for producing an alcohol compound comprising hydrogenating a ketone compound with the sulfonate catalyst according to claim 1 under pressurized hydrogen to produce the alcohol compound.

* * * * *